(12) United States Patent
McMichael

(10) Patent No.: US 6,294,171 B2
(45) Date of Patent: Sep. 25, 2001

(54) METHODS FOR TREATING DISEASE STATES COMPRISING ADMINISTRATION OF LOW LEVELS OF ANTIBODIES

(75) Inventor: John McMichael, Delanson, NY (US)

(73) Assignee: Milkhaus Laboratory, Inc., Delanson, NY (US)

( * ) Notice: Subject to any disclaimer, the term of this patent is extended or adjusted under 35 U.S.C. 154(b) by 0 days.

(21) Appl. No.: 09/774,770

(22) Filed: Jan. 31, 2001

Related U.S. Application Data

(63) Continuation-in-part of application No. 09/514,993, filed on Feb. 29, 2000, now Pat. No. 6,187,309.
(60) Provisional application No. 60/153,838, filed on Sep. 14, 1999.

(51) Int. Cl.[7] .......................... A61K 39/40; A61K 39/42
(52) U.S. Cl. .......................................... 424/150.1
(58) Field of Search ........................ 424/150.1, 159.1

(56) References Cited

U.S. PATENT DOCUMENTS

| 4,384,993 | * | 5/1983 | Sato et al. ............... | 260/112 B |
| 4,692,331 | * | 9/1987 | Uemaura et al. ............... | 424/85 |

* cited by examiner

*Primary Examiner*—Raymond Henley, III
(74) *Attorney, Agent, or Firm*—Marshall, Gerstein & Borun

(57) ABSTRACT

The invention provides methods and compositions for treating the symptoms of disease states associated with the presence of a toxin or infectious agent having the step of administering an antibody specific for the toxin or infectious agent at a dosage of less than 0.1 mg per day.

33 Claims, No Drawings

METHODS FOR TREATING DISEASE STATES COMPRISING ADMINISTRATION OF LOW LEVELS OF ANTIBODIES

This application is a continuation-in-part of U.S. patent application Ser. No. 09/514,993 filed Feb. 29, 2000 and issued Feb. 13, 2001 as U.S. Pat. No. 6,187,309 which claims benefit of U.S. Provisional Patent Application Ser. No. 60/153,838 filed Sep. 14, 1999 the disclosures of which are hereby incorporated by reference.

BACKGROUND OF THE INVENTION

The therapeutic use of antibodies is generally limited to: (a) imimunotherapy where a specific antibody directed against a discreet antigen is used to counter the effect of that antigen. Examples include using an antitoxin administered to neutralize a toxin, or antibody against an infectious agent to interrupt the pathophysiological process induced by that target organism; (b) the administration, often iv, of high levels of antibody (gamma globulin therapy) to compensate for transient or permanent immune deficiency; and (c) monoclonal antibody therapy to combat cancer, certain autoimmune disorders and metabolic diseases. In all these cases, antibody is provided in relatively high concentrations for the purpose of having that antibody combine directly with its target antigen to render that antigen inoperable, non-infectious or neutralized. For example, Gamnimune™ (Bayer Biological) contains 50 mg protein (immunoglobin) per mL and normal dosing can be up to 1000 mg/kg body weight. Ganunar—P™ I.V. (Aventis Behring) is administered at dosages up to 400 mg/kg body weight. Bayhep B™ (Hepatitis B knunoglobulin) (Bayer Biological) is 15–18% protein [immunoglobulin] is administered at dosages of up to 0.6 ml/kg body weight=0.01 g/kg =100 mg/kg. Further, hnogam Rabies—HT™ (Aventis Pasteur) is 10–18% protein and is administered at a dosage of 0.133 ml/kg (240 mg/kg) body weight.

Of interest to the present application is the disclosure of co-owned, allowed U.S. patent application Ser. No. 09/514,993 which is directed to the administration of anti-ruibeola antibodies for the treatment of symptoms of various central nervous system diseases including autism, multiple sclerosis, attention deficit disorder (ADD) and attention deficit hyperactivity disorder (ADHD). Examples therein emonstrated the efficacy of treating the symptoms of those disease states with dosages of from 0.1 mg to 1 mg of anti-rubeola antibody per dose.

While the administration of larger quantities of immunoglobulins is effective in the treatment of many disease states there remains a dosire in the art for alternative methods for treatment of disease states.

SUMMARY OF THE INVENTION

The present invention is directed to the discovery that the symptoms of disease states associated with the presence of a toxin or infectious agent may be effectively treated by administration of very low levels of antibodies specific for the toxin or infectious agent. The levels of antibodies admninistered are substantially lower than those traditionally administered to directly neutralize target antigens and for example are typically less than 0.1 mg of antibody per day. Specifically, the antibodies may be administered in one or in multiple dosages but the sum of antibodies administered in any 24 hour period is less than 0.1 mg.

While the antibody may be monoclonal or polyclonal, it is preferably monoclonal according to one aspect of the invention. The antibody may be admninistered by a variety of manners but is preferably administered enterically and most preferably orally. Suitable methods of oral administration include oral drench and sublingual administration. According to another preferred aspect of the invention the antibody is administered in an enterically protected form. In addition, the antibodies of the invention may be administered by injection such as by subcutaneous injection.

The symptoms of various disease states can be treated according to the invention including those of various central nervous disorders including autism, multiple sclerosis, attention deficit disorder (ADD), and attention deficit hyperactivity disorder (ADHD), all of which can be treated by administration of very low levels of anti-rubeola antibody. Dosages of antibodies administered according to the invention including anti-rubeola antibodies range from $1\times10^{-10}$ to a $1\times10^{-1}$ mg/dosage with dosages of from $1\times10^{-5}$ to $1\times10^{-4}$ mg (e.g. $8\times10^{-5}$ mg) and dosages of from $2\times10^{-5}$ to $2\times10^{-3}$ mg being preferred.

The invention also provides treatment of the symptoms of pulmonary infection by administering an effective amount of anti-Mycoplasma pneumonia antibody with daily dosages of less than 0.1 mg being preferred and daily dosages ranging from $1\times10^{-5}$ to $1\times10^{-3}$ mg/day being particularly preferred.

The invention also provides treatment of symptoms of Alzheimer's Disease by administering an effective amount of anti-amyloid beta antibodies with daily dosages of less than 0.1 mg being preferred and daily dosages ranging from $1\times10^{-5}$ to $1\times10^{31\ 3}$ being particularly preferred.

According to a further aspect of the invention it has been discovered that administration of anti-rubeola antibodies can be effective in the treatment of symptoms of Crohn's Disease. Accordingly, the invention provides a method of treating the symptoms of Crohn's Disease comprising administering an effective amount of anti-rubeola antibody. Preferred dosages are less than 0.1 mg antibody daily with daily dosages ranging from $2\times10^{-5}$ to $2\times10^{-3}$ mg being particularly preferred.

According to a further aspect of the invention it has been discovered that the administration of anti-Klebsiella pneumnonia antibodies can be useful for the treatment of rheumatoid arthritis and specifically for juvenile rheumatoid arthritis. Preferred dosages are less than 0.1 mg of anti-Klebsiella pneumonia antibody daily with daily dosages ranging from $1\times10^{-4}$ to $1\times10^{-3}$ mg/day (e.g. $4\times10^{-4}$ mg/day) being particularly preferred.

The invention also provides methods for treating the symptoms of diabetes comprising the method of administering an effective amount of antibody directed against glutamnic acid decarboxylase. Preferred dosages are less than 0.1 mg of anti-glutamic acid decarboxylase antibody daily with daily dosages ranging from $1\times10^{-4}$ to $1\times10^{-3}$ mg/day (e.g. $4\times10^{-4}$ mg/day) being particularly preferred.

The invention also provides pharmaceutical compositions for administration to subjects for treatment of the symptoms of disease states comprising antibody specific for a toxin or infectious agent associated with the disease state in a dosage unit of less than 0.1 mg antibody.

DETAILED DESCRIPTION

Without intending to be bound by any particular theory of the invention, it is believed that the invention described herein utilizes antibodies in remarkably low concentrations as molecular signals to induce a response similar or even superior to that seen with the traditional approach of introducing antibody at concentrations several logs greater than that associated with this invention. However, even though the concentrations of antibody are significantly different between traditional use and this invention, the specificity of the reaction remains intact. That is, low level of antibody directed against target A will react with target A but not B, unless B is antigenically closely related to A.

The similarity in responses between traditional gamma-globulin therapy and the invention, and the disparity of concentrations of antibody to induce the desired result, recalls the relationship in concentrations of antigen, or antigenic extract, used by allergists employing the maximum tolerated dose approach to hypersensitivity therapy and those using the neutralization method.

In the case of the present invention results similar to those obtained by traditional gamma globulin therapy are reached by an apparently different pathway. The traditional approach of using specific antibody in high concentration to treat or counter a specific antigen is well understood in that the antibody makes direct contact with its antigen target, combines with it, and alones or in the presence of other factors, such as the complement system, the antigen is destroyed or neutralized. The mechanism of action of the present invention whereby antigens are destroyed or neutralized by a pathway initiated by the presence of low levels of antibodies specific for the antigen is not completely understood but is the focus of ongoing research.

The invention described herein provides methods for treating ADD/ADHD, autism, MS, Crohn's Disease and related disorders. The invention describes the use of specific anti-rubeola antibody used a relatively low dose as a systemic signal to specifically inhibit virus replication or the body's aberrant response to the virus that results in the symptoms characteristic of the diseases.

Anti-rubeola antibody useful in practice of the invention may be obtained from a variety of sources. Suitable antibodies may be polyclonal or monoclonal and can be derived from various animal sources. A preferred anti-rubeola antibody for use in practice of the invention is polyvalent rabbit anti-rubeola antibody available from Cortex Biochemicals, San Leandro, Calif.

Antibodies specific for other antigens such as Klebsiella pneumonia, Mycoplasma pneumonia, chorionic gonadotropins, Amyloid-beta, and glutamic acid decarboxylase may be obtained from various commercial sources. A preferred source of antibody for Klebsiella pneumonia is Bio-Trend Chemikalien, Cologne, Germany and preferred anti-Mycoplasma pneumonia antibodies may be obtained from Cortex Biochemicals, San Leandro, Calif. Preferred sources of anti-amyloid-beta antibodies are Chemicon International Inc., Temecula, Calif. and Boeringer Manneim with preferred antibodies being those directed against human chorionic gonadotropin (hCG) holoprotein. A preferred antibody specific for glutamic acid decarboxylase is available from Chemicon International Inc., Temecula, Calif.

The following examples are illustrative and are not intended to limit either the scope or spirit of the invention.

EXAMPLE

Example I

According to this example, low dosages of anti-rubeola antibody were administered to an eight year old male subject exhibiting the symptoms of attention deficit disorder. Specifically, the subject was treated by sublingual administration once daily of one drop of a composition comprising $8 \times 10^{-5}$ mg of anti-rubeola antibody (Cortex Biochemicals, San Leandro, Calif.). The subject exhibited improvements in concentration and improved grades with some increase in activity in the evenings.

Example II

According to this example, a female subject in her mnid-thirties presented with a 12 year history of multiple sclerosis which primarily affected muscle control of her legs. The subject was treated by sublingual administration twice daily of one drop of a composition comprising $8 \times 10^{-5}$ mg of anti-rubeola antibody (Cortex Biochemicals, San Leandro, Calif.). After a period of three weeks, the subject exhibited improved motor control and was capable of driving an automobile for the first time in years.

Example III

According to this example, four dogs presenting with progressive central nervous system pathology and exhibiting symptoms similar to those of multiple sclerosis were treated by administration of $8 \times 10^{-5}$ mg per day dosages of anti-rubeola antibodies by subcutaneous injection. The animals were treated over a period of eight months and were either stable or slowly improving with respect to their condition.

Example IV

According to this example, human patients presenting with cancer of various types (pancreatic, lung and colon) are treated by two to four times daily sublingual administration of $8 \times 10^{-5}$ mg polyclonal anti-hCG antibodies derived from rabbits (Cortex Biochemicals, San Leandro Calif.)

Example V

According to this example, four dogs suffering with osteosarcoma were treated by subcutaneous injection of $3.2 \times 10^{-5}$ mg per day of anti-hCG antibody. Canine osteosarcoma usually metastisizes from the bone to the lungs and animals similarly afflicted typically have a lifespan of six-months. After five months of treatment the dogs do not exhibit signs of metastisis and appear in healthy condition as evidenced by coat condition, appetite, attitude and quality of life.

Example VI

According to this example two patients aged 8 and 9 presented with severe juvenile rheumatoid arthritis and were treated by sublingual administration twice daily of $8 \times 10^{-5}$ mg of antibodies specific for Klebsiella pneumonia obtained from Bio-Trend Chemikalien, Cologne, Germany. Prior to being treated the subjects suffered from pain, restricted range of motion, and joints which were swollen and sore. After one week of treatment according to the methods of the invention, pain and swelling were reduced and the range of movement was increased. Optimnum concentration of antibody per dose has been approximately $4 \times 10^{-4}$ mg.

Example VII

According to this example, a patient presented with chronic pulmonary infections and fibrosis exhibiting symptoms of shortness or breath, chest pain and decreased stamina. The subject was treated by sublingual administration twice daily of $8 \times 10^{-5}$ mg of antibody to Mycoplasma pneumonia (Biochemicals, San Leandro, Calif.). The subject reported a positive response within 7 days, as evidenced by decreased shortness of breath, decreased chest pain, decreased edema, increased stamina and ability to carry out normal activities of daily living.

Example VIII

According to this example, five patients presented with the symptoms of Alzheimer's disease and were treated by sublingual administration of four drops daily of a composition comprising $5 \times 10^{-6}$ mg of anti-ainyloid beta antibodies (Boeringer Mannheim). At four weeks after treatmnent, three of the patients did not exhibit any effects but one patient reported having an improved pattern of speech as words came easier to her. The fifth subject reported that after two weeks she was no longer "struggling to remember things."

According to this example five senile dogs were treated by subcutaneous administration with $5 \times 10^{-6}$ mg of anti-amyloid beta antibodies. All the dogs responded positively after two weeks of daily treatment and were more active and interacted more appropriately with their masters.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

What is claimed is:

1. A method of treating the symptoms of a disease state associated with the presence of a toxin or infectious agent comprising the step of administering an antibody specific for said toxin or infectious agent at a dosage of less than 0.1 mg per day.

2. The method of claim 1 wherein the antibody is a monoclonal antibody.

3. The method of claim 1 wherein the antibody is administered orally.

4. The method of claim 3 wherein the antibody is administered by oral drench.

5. The method of claim 3 wherein the antibody is administered sublingually.

6. The method of claim 3 wherein the antibody is administered in an enterically protected form.

7. The method of claim 1 wherein the antibody is admninistered by injection.

8. The method of claim 7 wherein the antibody is admninistered by subcutaneous injection.

9. The method of claim 1 wherein the disease state is autism and the method comprises administering an effective amount of anti-rubeola antibody.

10. The method of claim 9 wherein the anti-rubeola antibody is administered at a dosage of from $6 \times 10^{-7}$ to $8 \times 10^{-5}$ mg per day.

11. The method of claim 1 wherein the disease state is multiple sclerosis and the method comprises administering an effective amount of anti-rubeola.

12. The method of claim 11 wherein the anti-rubeola antibody is administered at a dosage of from $2 \times 10^{-5}$ to $2 \times 10^{-3}$ mg per day.

13. The method of claim 1 wherein the disease state is selected from the group consisting of attention deficit disorder (ADD) and attention deficit hyperactivity disorder (ADHD) and the method comprises administering an effective amount of anti-rubeola antibody.

14. The method of claim 13 wherein the anti-rubeola antibody is administered at a dosage of from $1 \times 10^{-5}$ to $1 \times 10^{-4}$ mg per day.

15. The method of claim 1 wherein the disease state is cancer and the method comprises administering an effective amount of anti-chorionic gonadotropin antibody.

16. The method of claim 15 wherein the antibody is hCG.

17. The method of claim 15 wherein the anti-chorionic gonadotropin antibody is administered as a dosage of from $1 \times 10^{-5}$ to $1 \times 10^{-4}$ mg per day.

18. The method of claim 15 wherein the cancer is a sarcoma.

19. The method of claim 15 wherein the cancer is an osteosarcoma.

20. The method of claim 1 wherein the disease state is pulmonary infection and the method comprises administering an effective amount of anti-Mycoplasma pneumonia antibody.

21. The method of claim 20 wherein the anti-Mycoplasma pneumonia antibody is administered at a dosage of from $1 \times 10^{-5}$ to $1 \times 10^{-4}$ mg per day.

22. The method of claim 1 wherein the disease state is Alzheimer's Disease and the method comprises administering anl effective amount of anti-amyloid beta antibody.

23. The method of claim 22 wherein the anti-amyloid-beta antibody is administered at a dosage of from $1 \times 10^{-5}$ to $1 \times 10^{-4}$ mg per day.

24. A method of treating the symptoms of diabetes comprising administering an effective amount of anti-glutamic acid decarboxylase antibody.

25. The method of claim 24 wherein the anti-glutamic acid decarboxylase antibody is administered at a dosage of less than 0.1 mg per day.

26. The method of claim 24 wherein the anti-glutainic acid antibody is administered at a dosage of from $1 \times 10^{-5}$ to $1 \times 10^{-4}$ mg per day.

27. A method of treating symptoms of Crohn's Disease comprising the step of admninistering an effective amount of anti-rubeola antibody.

28. The method of claim 27 wherein the anti-rubeola antibody is administered at a dosage of less than 0.1 mg per day.

29. The method of claim 27 wherein the anti-rubeola antibody is administered at a dosage of $1 \times 10^{-5}$ to $1 \times 10^{-4}$ mg per day.

30. A method of treating symptoms of rheumatoid arthritis comprising the step of administering an effective amount of anti-Klebsiella pneumonia antibody.

31. The method of claim 30 wherein the anti-Klebsiella pneumonia antibody is administered at a dosage of less than 0.1 mg per day.

32. The method of claim 30 wherein the anti-Klebsiella pneumonia antibody is administered at a dosage of from $1 \times 10^{-4}$ to $1 \times 10^{-3}$ mg per day.

33. A pharmaceutical composition for administration to a subject for treatment of a disease state comprising antibody specific for a toxin or infectious agent associated with the disease stato in a dosage unit of less than 0.1 mg antibody.

* * * * *

UNITED STATES PATENT AND TRADEMARK OFFICE
CERTIFICATE OF CORRECTION

PATENT NO. : 6,294,171 B2
DATED : September 25, 2001
INVENTOR(S) : McMichael

Page 1 of 1

It is certified that error appears in the above-identified patent and that said Letters Patent is hereby corrected as shown below:

Column 6,
Line 60, replace "stato" with -- state --

Signed and Sealed this

Twenty-eighth Day of May, 2002

Attest:

Attesting Officer

JAMES E. ROGAN
Director of the United States Patent and Trademark Office